United States Patent [19]
Bakich et al.

[11] Patent Number: 5,928,889
[45] Date of Patent: Jul. 27, 1999

[54] PROTOCOL FOR SIMULATED NATURAL BIOFILM FORMATION

[75] Inventors: Shannon L. Bakich, Racine; Mark M. Gipp, Mount Pleasant, both of Wis.

[73] Assignee: S.C. Johnson & Son, Inc., Racine, Wis.

[21] Appl. No.: 09/023,520

[22] Filed: Feb. 13, 1998

[51] Int. Cl.⁶ ............................... C12Q 1/02; G01N 33/53
[52] U.S. Cl. ........................ 435/29; 435/289.1; 435/970
[58] Field of Search ................................. 435/29, 289.1, 435/970

[56] References Cited

U.S. PATENT DOCUMENTS

| | | | |
|---|---|---|---|
| 3,198,005 | 8/1965 | Wolfson | 435/29 |
| 4,631,961 | 12/1986 | Yohe et al. | 435/29 |
| 4,945,758 | 8/1990 | Carpenter | 435/29 |
| 5,049,492 | 9/1991 | Sauer et al. | 435/29 |
| 5,246,560 | 9/1993 | Nekoksa et al. | 435/29 |
| 5,349,874 | 9/1994 | Schapira et al. | 435/29 |
| 5,356,521 | 10/1994 | Nekoksa et al. | 435/29 |
| 5,488,856 | 2/1996 | Dirk | 435/29 |
| 5,599,451 | 2/1997 | Guiot | 435/29 |
| 5,605,836 | 2/1997 | Chen et al. | 435/29 |
| 5,709,546 | 1/1998 | Waggoner | 435/29 |

OTHER PUBLICATIONS

Biofilm Formation in the Industry: A Review, *Food Reviews International*, 8(4), 573–603 (1992); Tiina Mattila–Sandholm & Gun Wirtanen.

Biofilms: Structure and Organisation, *Microbial Ecology in Health and Disease*, vol. 8: 305–308 (1995). J. Wimpenny.

Microbial Biofilms, *Annu. Rev. Microbial*, 1995, 49: 711–45, J. W. Costerton & Zbigniew Lewandowski; D. E. Caldwell & D. R. Korber; H. M. Lappin–Scott.

Effect of Growth Conditions and Substratum Composition on the Persistence of Coliforms in Mixed–Population Biofilms, *Applied & Environmental Microbiology*, Nov. 1996, pp. 4014–4018, A.K. Camper, W. L. Jones & J. T. Hayes.

Biofilm Structure Heterogeneity Visualized by Three Microscopic Methods, Wat. Res. vol. 29, No. 8, pp. 2006–2009, 1995, P. S. Stewart, R. Murga, R. Sprinivasan & D. deBeer Overview of Microbial Biofilms, *Jrnl. of Industrial Microbiology* (1995) 15, 137–140 J. W. Costerton.

Uptake and Release of Insert Fluorescence Particles by Mixed Population Biofilms, *Biotechnology & Bioengineering*, vol. 53, No. 5 1997, pp. 459–469, S. Okabek, T. Yasuda & Y. Watanabe.

Neu et al; FEMS Microbiology Ecology 24; (1997) pp. 11–25, Month not available.

*Primary Examiner*—Louise N. Leary

[57] ABSTRACT

This invention provides a methodology for controlled biofilm formation in accordance with a monitored protocol. In a typical embodiment, a natural biofilm inoculum is used to form a simulated natural biofilm on retrievable slides in an annular reactor. The monitored protocol in the annular reactor subjects the bacterial consortia of the simulated natural biofilm to simulated environmental conditions. The invention simulated natural biofilm on a slide surface has utility for the testing of formulated product activity for inhibition or removal of the simulated natural biofilm, thereby providing a reliable indicator of the relative activity of the products under natural environmental conditions.

20 Claims, No Drawings

PROTOCOL FOR SIMULATED NATURAL BIOFILM FORMATION

BACKGROUND OF THE INVENTION

This invention generally relates to methodology for production of experimental biofilm matrices on selected surfaces. More specifically this invention relates to the production of simulated natural biofilms for testing the activities of formulated products for inhibition or removal of the simulated biofilms from a support surface.

Since 1943 a vast technical literature has developed in connection with advances in biofilm research. The understanding of biofilm processes has progressed rapidly in the last decade. One of the ultimate goals in studying biofilms is to evolve means for manipulating these processes for technological and ecological advantage. Biofilm science is reviewed in publications such as Food Reviews International, 8 (4), 573 (1992); Microbial Ecology in Health and Disease, 8, 305 (1995); Annu. Rev. Microbial, 49, 711 (1995); Applied and Environmental Microbiology, 4014 (November 1996); and "Biofilms" by W. G. Characklis and K. C. Marshall (John Wiley & Sons, Inc., New York, 1989).

As elaborated in the technical literature, a biofilm consists of cells immobilized on a substratum and embedded in an organic polymer matrix of microbial origin. A biofilm is a surface accumulation, which is not necessarily uniform in time or space. A biofilm may be composed of a significant fraction of inorganic or abiotic substances held cohesively by the biotic matrix. A biofilm is a protective matrix for bacteria, with the essential purpose of survival in an environment of limited nutrient supply.

Biofilms consist of both host microbes and their extracellular products, usually exopolysaccharides. Microbes have a tendency to form these protective exopolysaccharide matrices after they have adhered to a surface. The formation of biofilm complexes requires only humid conditions and/or water systems and contact with a support surface. With respect to nutrients, a nutrient deficiency in fact may increase the biofilm formation capacity of microbes, as reported in Adv. Appl. Microbiol., 29, 93 (1983).

Biofilms generally can be produced by almost all microbes under suitable conditions. The most common biofilm producers belong to the genera Pseudomonas, Enterobacter, Flavobacterium, Alcaligenes, Staphylococcus, and Bacillus. There also are anaerobes that can construct corrosive biofilms.

Besides causing problems in cleaning and hygiene, biofilms can cause energy losses and blockages in condenser and heat exchange tubes, interfere with water and waste water systems, and form drag-inducing encrustations on ship hulls. In the medical disciplines, a biofilm (referred to as "glycocalyx") formed by bacteria such as a Pseudomonas species can be the systemic causation of diseases of the lungs or the gastrointestinal and urinary tracts. Additionally, a biofilm formed by bacteria such as Staphylococcus species can be a serious contamination problem in foreign-body instruments such as cardiac pacemakers, catheters, prostheses, artificial valves, and the like. Dental plaque is also a typical form of biofilm.

One of the main purposes of natural biofilm formation is for the protection of the host microbes from a hostile environment. As a consequence, there is a combative interaction between microbes in biofilms and biocidal vehicles such as preservatives, disinfectants and antibiotics. Further, the sessile mode of bacterial growth in biofilms differs from that of the same bacteria species that are present as planktonic cells in a circulating aqueous medium which interfaces with the biofilm. Biofilms also act as a trap for nutrient acquisition, which is an important factor when bacteria grow on surfaces and the nutrient supply is oligotrophic.

Because of the manifold ramifications of biofilm formation, there is a serious commitment to biofilm research in a broad range of scientific investigations. Methods of studying biofilm formation include microbiological, physical, and chemical methods. When microbes from extreme natural environments are cultured, standard plate counts usually do not provide accurate estimates. Thus, the classical evaluation methods relying on microbiological plating have questionable value with respect to the laboratory study of biofilms which are intended to achieve authentic correspondence with natural biofilms which exist in the biosphere. In addition, formation of a natural type biofilm in the laboratory environment is difficult, mainly because there are no standardized methodologies currently available.

There is increasing interest in the research and development of methodologies for the production and study of biofilms in a laboratory environment. Accordingly, it is an object of this invention to provide an improved method for the laboratory production of biofilms which simulate natural biofilms that grow under biospheric conditions.

It is another object of this invention to provide a laboratory protocol for simulated natural biofilm production, in combination with a further protocol for testing the activities of formulated products for inhibition or removal of the simulated biofilms as a reliable indicator of the same activities under natural environmental conditions.

Other objects and advantages of the present invention shall become apparent from the accompanying description and examples.

Publications of background interest with respect to the present invention include Wat. Res., 22 (8), 2006 (1995); J. Ind. Microbial., 15, 137 (1995); and references cited therein; incorporated herein by reference.

DESCRIPTION OF THE INVENTION

One or more objects of the present invention are accomplished by the provision of a method for controlled biofilm formation in accordance with a monitored protocol which comprises (1) arranging at least one removable slide within the internal reservoir of a reactor; (2) introducing a bacterial inoculum and aqueous nutrient medium into the reservoir; (3) providing the aqueous suspension medium with agitation for an incubation period sufficient to initiate bacterial attachment to the slide surface; (4) draining the suspension medium from the reservoir; (5) recharging the reservoir with aqueous nutrient medium to maintain bacterial growth for an elapsed time period sufficient to establish a biofilm of prescribed thickness on the slide surface; and (6) retrieving the slide from the reservoir, and optionally determining the population of bacterial Colony Forming Units per square centimeter of the biofilm on the slide surface.

A suitable laboratory scale reactor can comprise an annular reactor which has dimensions between about 2–30 centimeters in diameter and 5–50 centimeters in height. A preferred type of reactor is one constructed of polycarbonate, with a rotating inner drum which is adapted to secure stainless steel type retrievable slides. Annular reactors are commercially available products, such as the annular reactors sold by Biosurface Technologies, Corp., Bozeman, Mont.

In another embodiment this invention provides a method for controlled biofilm formation in accordance with a monitored protocol which comprises (1) arranging removable slides within the internal reservoir of a reactor; (2) introducing a bacterial inoculum and aqueous nutrient medium into the reservoir; (3) providing the aqueous suspension medium with agitation for an incubation period sufficient to initiate bacterial attachment to the slide surfaces; (4) draining the suspension medium from the reservoir; (5) recharging the reservoir with aqueous nutrient medium at least once every 24 hours of elapsed time period; (6) repeating the step (5) regimen for an extended period sufficient to establish a biofilm of prescribed thickness on the slide surfaces; and (7) retrieving the slides from the reservoir, and optionally determining the population of bacterial Colony Forming Units per square centimeter of the biofilm on the slide surfaces.

A standardized Mineral Salts nutrient medium can be employed for the biofilm bacterial growth cycles. Suitable nutrient media for biofilm formation are described in technical publications such as Biotechnol. Bioeng., 53 (5), 459 (1997); incorporated herein by reference. A typical nutrient medium contains sources of carbon, nitrogen, phosphate and trace nutrients.

In a preferred embodiment, the bacterial inoculum is derived from a natural biofilm. This is illustrated by a bacterial inoculum which is extracted from a household drain biofilm. The monitored protocol in the reactor is designed to provide essential correspondence with simulated household drain conditions, thereby promoting the formation of a simulated biofilm in the reactor which has close correspondence with a household drain natural biofilm.

The term "simulated biofilm" as employed herein refers to a derivative biofilm which has essential phenotypic correspondence with the bacterial consortia of its sampled natural biofilm.

The term "natural biofilm" as employed herein refers to a biospheric surface-mediated bacterial consortium which is in a dynamic relationship with environmental parameters.

The present invention methodology has particular advantage for the preparation of simulated biofilms which are a convenient and reliable vehicle for testing the activities of formulated products, where said products are intended for inhibition or removal of natural biofilms having a derivative relationship with the simulated biofilms respectively.

The present invention methodology can be illustrated by reference to a simulated household drain biofilm which is derived from an inoculum of a natural household drain biofilm.

In practice, the inoculum and aqueous nutrient medium are introduced into an annular reactor which holds a set of stainless steel slides. The reactor contents are incubated for between about 4–60 hours at a temperature between about 15°–45° C.

The reactor reservoir is drained and recharged with aqueous nutrient medium at least once every 48 hours, over an elapsed time period of at least about 72 hours. Preferably, the reservoir is drained and recharged at least twice every 24 hours, over an elapsed time period between about 2–45 days.

Simulated biofilm growth on the slide surfaces in the annular reactor is continued until a desired biofilm thickness is achieved, e.g., between about 10–500 microns. The biotic population in a simulated biofilm typically will be between about $10^5$–$10^{15}$ bacterial Colony Forming Units per square centimeter ($CFU/cm^2$) on the slide surfaces.

The methodology of the present invention has general utility for the production of simulated biofilms which are intended for application in a further protocol for testing the activity of an experimental product or a commercial product. The further protocol can include testing the activity of products such as biocides and cleaners, and products for opening conduits which are clogged with biomass, and the like.

The following examples are further illustrative of this present invention. The components and specific ingredients are presented as being typical, and various modifications can be derived in view of the foregoing disclosure within the scope of the invention.

EXAMPLE I

This Example illustrates invention methodology for growing a simulated biofilm, as derived from a household drain natural biofilm inoculum, in an annular reactor under simulated household drain conditions.

An annular reactor with a rotatable inner drum is utilized (Biosurface Technologies, Corp.; Bozeman, Mont.). The reactor has a 23 cm height and a 13 cm diameter, and is constructed of autoclavable polycarbonate. The reactor is adapted to secure the 12 stainless steel slides which are employed in the protocol.

A biofilm sample is extracted from a household drain, and used as the protocol inoculum.

An aqueous nutrient medium is employed which has the following composition:

0.2% yeast extract
0.2% Trypticase soy broth
0.1% kaolin solution
7 g/L $K_2HPO_4$
3 g/L $KH_2PO_4$
1 g/L $(NH_4)_2SO_4$
0.1 g/L Mg $SO_4$·$7H_2O$
warm water (28°–32° C.)

A sample of men's shaving residue is added to the reactor about every 24 hours with the nutrient medium. The residue contains EDGE® shaving cream, water, hair, and skin cells.

The protocol is conducted in the following manner:

(1) a loop of homogenized household drain biofilm is suspended in each of two flasks (100 ml of Trypticase soy broth respectively), and incubated for two days at 37° C. in a shaking incubator;

(2) one ml of suspended bacteria from each flask is inoculated into a second flask (100 ml of Trypticase soy broth), and incubated with agitation for two days at 37° C.;

(3) the suspension contents of one of the two flasks is charged to the annular reactor;

(4) nutrient medium and warm water (about 800 ml) are added to the annular reactor, which submerges 12 removable stainless steel slides that are secured to the inner drum surface, and the rotation of the inner drum is commenced;

(5) the reactor contents are incubated for two days at room temperature;

(6) the reactor liquid volume is drained, and the reactor is refilled with nutrient medium and shaving residue;

(7) the step (6) drain and refill procedure is repeated two times per 24 hours to simulate household drain usage, and the procedure is continued for a time period between about 4–6 weeks sufficient to develop a 40–50 micron thick biofilm on the stainless steel slides ($10^9$–$10^2$ Colony Forming Units per square centimeter);

(8) the stainless steel slides are retrieved, which have an attached biofilm with a bacterial community that has prototypic correspondence with the environmental consortia of the originally sampled natural household drain biofilm; and (9) the biofilm-coated slides are utilized in a further protocol to test the activities of laboratory formulations and commercial products.

EXAMPLE II

This Example illustrates a method for determining the Colony Forming Units per square centimeter (CFU/cm$^2$) on biofilm-coated slides.

A stainless slide retrieved from the annular reactor in Example I is placed in a beaker with 10 ml of PBS nutrient medium. The slide is scraped from top to bottom using a sterile cell scraper to provide a biofilm sample. The sample is homogenized one minute with a tissumizer operating at moderate speed.

One ml of the homogenized biofilm sample is diluted in 9 ml of PBS medium. The resulting 10 ml sample is vortexed, and then the sample is diluted serially. A 0.1 ml quantity of a diluted sample is plated on R2A agar. Each sample dilution is plated in triplicate.

The dilution sample on each plate is spread with a plate spreader, and the plates are incubated at room temperature for five days.

A plated sample which has approximately 30–300 colonies is counted. The colony counts, dilution, and the scraped area of the slide is used to determine CFU/cm$^2$.

EXAMPLE III

This Example illustrates a method for testing the activities of household drain care products on laboratory-grown biofilms which simulate natural household drain biofilms.

A sink and drain system is assembled from three 6" straight sections of 1.25" (I.D.) glass pipe, one 1.25" (I.D.) glass P-trap, and one 1.25 (I.D.) glass down-pipe section.

The drain system is flushed with one gallon of water (38° C.).

One biofilm-coated slide in accordance with the Example I protocol is secured to the top of the horizontal glass pipe section after the P-trap, and another biofilm-coated slide is secured to the bottom of the horizontal glass pipe section after the P-trap.

A household drain-care product is dispensed into the drain system, and the product is maintained in the drain system for 8 hours. The drain system then is gently rinsed with one gallon of water (38° C.).

The treated slides are removed and placed into wells of a slotted tray. The slides are submerged in 5% sodium thiosulfate solution for two minutes, and then transferred to a second tray with deionized water. The CFU/cm$^2$ are determined, and compared with the initial count of control samples.

Following the above-described procedures, the activity of an experimental drain-care product, Formulation DC-X, is tested in comparison with a commercial drain-care product, PS Liquid Plumr®. The results of the comparative test are summarized in TABLES I-II.

TABLE I

| Treatment | Last Square Mean (LOG CFU*) |
| --- | --- |
| Control | 9.00 A |
| Plumr (top slide) | 7.72 B |
| DC-X (top slide) | 4.43 C |

TABLE I-continued

| Treatment | Last Square Mean (LOG CFU*) |
| --- | --- |
| DC-X (bottom slide) | 3.76 Cd |
| Plumr (bottom slide) | 3.68 Cd |

*ABC/abcd: Means with the same letter are not significantly different at 95/90% confidence level.

TABLE II

| | Test vs. Control Difference (Log CFU) Difference (prob) | | | |
| --- | --- | --- | --- | --- |
| | Plumr Bottom | DC-X Top | DC-X Bottom | Plumr Top |
| Control | 5.32 (.01) | 4.66 | 5.24 (0.1) | 1.28 (.10) |
| DC-X Top Slide | .67 (.06) | | .58 (.10) | 3.38 (.10) |
| DC-X Bottom Slide | .08 (nsd) | | | 3.96 (.01) |
| Plumr Top Slide | 4.05 (.01) | | | |

The comparative data indicate that Formulation DC-X effectively treats a greater biofilm surface area than the PS Liquid Plumr product. Formulation DC-X removes more biofilm than Plumr on the top slide in the drain system, as determined by the remaining CFU/cm$^2$ count on the slide. With respect to the bottom slide in the drain system, DC-X and Plumr are equally effective.

Top and bottom slides treated with DC-X have similar reduction in the amount of biofilm, while the top slide treated with Plumr has less reduction than the bottom slide treated with Plumr.

The differences indicated by the comparative data are statistically significant (95% confidence level), and microbiologically significant. Specifically, the differences observed are greater than a 2 log reduction in the amount of biofilm, which is significant in terms of microbiological observations in the biospheric environment.

What is claimed is:

1. A method for controlling biofilm formation in accordance with a monitored protocol which comprises (1) arranging at least one removable slide within the internal reservoir of a reactor; (2) introducing a bacterial inoculum an aqueous nutrient medium into the reservoir; (3) providing the aqueous suspension medium with agitation for an incubation period sufficient to initiate bacterial attachment to the slide surface; (4) draining the suspension medium from the reservoir; (5) recharging the reservoir with aqueous nutrient medium to maintain bacterial growth for an elapsed time period sufficient to establish a biofilm of prescribed thickness on the slide surface; (6) retrieving the slide from the reservoir, and optionally determining the population of bacterial Colony Forming Units per square centimeter of the biofilm on the slide surface; (7) placing the slide at a location designed to mimic a natural site of biofilm formation and (8) examining the effect of test biocide or cleaning formulations on the biofilm.

2. The method in accordance with claim 1 wherein the reactor is annular and has dimensions between about 2–30 centimeters in diameter and 5–50 centimeters in height.

3. The method in accordance with claim 1 wherein multiple stainless steel slides are arranged in the reservoir in step (1).

4. The method in accordance with claim 1 wherein the bacterial inoculum is derived from a natural biofilm.

5. The method in accordance with claim 1 wherein the bacterial inoculum is derived from a household drain biofilm, and the monitored protocol in the reactor corresponds to simulated household drain conditions.

6. The method in accordance with claim 1 wherein the aqueous nutrient medium comprises yeast, peptone and mineral salt ingredients.

7. The method in accordance with claim 1 wherein the step (3) incubation is for a period between about 40–60 hours at a temperature between about 15°–45° C.

8. The method in accordance with claim 1 wherein the reactor reservoir in step (5) is drained and recharged with aqueous nutrient medium at least once every 48 hours of elapsed time period.

9. The method in accordance with claim 1 wherein the step (5) elapsed time period is at least about 72 hours.

10. The method in accordance with claim 1 wherein the established biofilm in step (5) has a thickness between about 10–500 microns on the slide surfaces.

11. The method in accordance with claim 1 wherein the established biofilm in step (5) has a population between about $10^5$–$10^{15}$ bacterial Colony Forming Units per square centimeter on the slide surfaces.

12. The method in accordance with claim 1 wherein the biofilm-coated slide is utilized in a further protocol for testing the activity of a product for opening conduits which are clogged with biomass.

13. A method for controlling biofilm formation in accordance with a monitored protocol which comprises (1) arranging removable slides within the internal reservoir of a reactor; (2) introducing a bacterial inoculum and aqueous nutrient medium into the reservoir; (3) providing the aqueous suspension medium with agitation for an incubation period sufficient to initiate bacterial attachment to the slide surface; (4) draining the suspension medium from the reservoir; (5) recharging the reservoir with aqueous nutrient medium at least once every 24 hours of elapsed time period; (6) repeating the step (5) regimen for an extended period sufficient to establish a biofilm of prescribed thickness on the slide surfaces; (7) retrieving the slides from the reservoir, and optionally determining the population of bacterial Colony Forming Units per square centimeter of the biofilm on the slide surfaces; (8) placing the slide at a location designed to mimic natural site of biofilm formation and (9) examining the effect of test biocide or cleaning formulations on the biofilm.

14. The method in accordance with claim 13 wherein the bacterial inoculum is derived from a natural biofilm.

15. The method in accordance with claim 13 wherein the bacterial inoculum is derived from a household drain biofilm, and the monitored protocol in the reactor corresponds to simulated household drain conditions.

16. The method in accordance with claim 13 wherein the reservoir in step (5) is drained and recharged with aqueous nutrient medium at least twice every 24 hours, over an elapsed time period between about 2–45 days.

17. The method in accordance with claim 13 wherein the biofilm-coated slide is utilized in a further protocol for testing the activity of a product.

18. The method in accordance with claim 13 wherein the biofilm-coated slide is utilized in a further protocol for testing the activity of a product for opening conduits which are clogged with biomass.

19. A biofilm-coated slide produced in accordance with the method of claim 1.

20. A biofilm-coated slide produced in accordance with the method of claim 13.

* * * * *